US012201562B1

(12) United States Patent
Li et al.

(10) Patent No.: US 12,201,562 B1
(45) Date of Patent: Jan. 21, 2025

(54) PROTECTIVE ISOLATION HOOD

(71) Applicant: NINGBO CAREFUL SPECIAL CARS CO., LTD, Zhejiang (CN)

(72) Inventors: Weiding Li, Zhejiang (CN); Hongzhao Zhao, Zhejiang (CN); Yinzong Bao, Zhejiang (CN)

(73) Assignee: NINGBO CAREFUL SPECIAL CARS CO., LTD, Zhejiang (CN)

( * ) Notice: Subject to any disclaimer, the term of this patent is extended or adjusted under 35 U.S.C. 154(b) by 0 days.

(21) Appl. No.: 18/726,793

(22) PCT Filed: Mar. 9, 2023

(86) PCT No.: PCT/CN2023/080585
§ 371 (c)(1),
(2) Date: Jul. 4, 2024

(87) PCT Pub. No.: WO2023/174156
PCT Pub. Date: Sep. 21, 2023

(30) Foreign Application Priority Data

Mar. 15, 2022 (CN) .......................... 202210253667.7

(51) Int. Cl.
*B01D 46/00* (2022.01)
*A61G 1/04* (2006.01)
(Continued)

(52) U.S. Cl.
CPC ............. *A61G 10/005* (2013.01); *A61G 1/04* (2013.01); *A61G 7/0526* (2013.01); *A61L 9/16* (2013.01);
(Continued)

(58) Field of Classification Search
CPC ............... B01D 46/10; B01D 2209/14; B01D 2273/30; B01D 2279/35; B01D 2279/65;
(Continued)

(56) References Cited

U.S. PATENT DOCUMENTS 5,010,777 A * 4/1991 Yehl .......................... B60H 3/00
361/231
5,730,765 A * 3/1998 Henry ....................... B01L 1/02
55/385.2
(Continued)

FOREIGN PATENT DOCUMENTS

CN 101697933 A 4/2010
CN 210933492 U 7/2020
(Continued)

OTHER PUBLICATIONS

PCT/CN2023/080585 Written Opinion of the International Search Authority, May 25, 2023, pp. 1-4, original Chinese.
(Continued)

*Primary Examiner* — Minh Chau T Pham
(74) *Attorney, Agent, or Firm* — Addison D. Ault; IPGentleman Intellectual Property Services, LLC

(57) ABSTRACT

The present disclosure relates to a protective isolation hood for safe transportation of subjects, comprising a fixed base cover, a rotating auxiliary cover, a base cover sliding seat and a guide rail supporting base. The guide rail supporting base is connected to the base cover sliding seat, the fixed base cover is disposed on the base cover sliding seat, and the rotating auxiliary cover is rotationally arranged on the fixed base cover. A first isolation soft film is arranged at the end of the rotating auxiliary cover away from the fixed base cover, and the fixed base cover, the rotating auxiliary cover and the first isolation soft film constitute a protection space. A filter box is arranged on the fixed base cover, is located in the protection space, and is provided with a disinfection filter screen. The protective isolation hood enables isolation to be maintained throughout transportation of the subject.

8 Claims, 4 Drawing Sheets

(51) Int. Cl.
    *A61G 7/05*       (2006.01)
    *A61G 10/00*     (2006.01)
    *A61L 9/16*       (2006.01)
    *B01D 46/10*     (2006.01)

(52) U.S. Cl.
    CPC ..... *B01D 46/0028* (2013.01); *B01D 46/0045* (2013.01); *B01D 46/10* (2013.01); *A61L 2209/14* (2013.01); *A61L 2209/15* (2013.01); *B01D 2273/30* (2013.01); *B01D 2279/35* (2013.01); *B01D 2279/65* (2013.01)

(58) Field of Classification Search
    CPC ...... A61G 10/005; A61G 1/04; A61G 7/0526; A61G 2209/15; A61G 10/00; A61G 7/05
    USPC ......................... 55/385.1, 385.2; 128/201.25
    See application file for complete search history.

(56) References Cited

U.S. PATENT DOCUMENTS

| | | | | |
|---|---|---|---|---|
| 6,508,850 B1 * | 1/2003 | Kotliar | ................ | A61G 10/005 55/385.2 |
| 6,711,748 B2 * | 3/2004 | Paris | ................ | A41D 13/1209 2/422 |
| 6,826,783 B1 * | 12/2004 | Grove | ................ | A42B 3/10 128/201.25 |
| 6,916,238 B2 * | 7/2005 | Korman | ................ | F24F 3/163 55/385.2 |
| 6,918,141 B2 * | 7/2005 | Green | ................ | A42B 3/10 128/201.25 |
| 8,414,671 B2 * | 4/2013 | Augustine | ............ | A61G 13/108 55/467 |
| 11,337,876 B2 * | 5/2022 | Bryant | ................ | A61G 7/05 |
| 11,779,781 B2 * | 10/2023 | Anvari | ................ | A62B 7/10 128/205.12 |
| 11,931,607 B2 * | 3/2024 | Anvari | ................ | A62B 9/00 |
| 2008/0020695 A1 * | 1/2008 | Chang | ................ | B08B 15/026 55/385.2 |
| 2021/0353484 A1 | 11/2021 | Yu et al. | | |

FOREIGN PATENT DOCUMENTS

| | | |
|---|---|---|
| CN | 215961870 U | 3/2022 |
| CN | 114587848 A | 6/2022 |

OTHER PUBLICATIONS

PCT/CN2023/080585 Written Opinion of the International Search Authority, May 25, 2023, pp. 1-3, English translation accessed from WIPO on Jul. 3, 2024.

PCT/CN2023/080585 International Search Report, original Chinese, Mar. 15, 2022, pp. 1-3, original Chinese.

PCT/CN2023/080585 International Search Report, Mar. 15, 2022, pp. 1-2, English translation accessed from WIPO on Jul. 3, 2024.

* cited by examiner

PROTECTIVE ISOLATION HOOD

CROSS-REFERENCE TO RELATED APPLICATION

This application is a Section 371 National Stage Application of International Application No. PCT/CN2023/080585, filed on Mar. 9, 2023, entitled "PROTECTIVE ISOLATION HOOD", which claims priority to Chinese Application No. CN 202210253667.7, filed on Mar. 15, 2022, incorporated herein by reference in their entirety.

TECHNICAL FIELD

The present disclosure relates to the field of protective hoods, and in particular to a protective isolation hood.

BACKGROUND

Effective protection during the pandemic is the most effective, important and necessary measure to prevent the spread and infection of the virus in addition to medical treatment measures. In the wake of the combination of the SARS virus outbreak in 2003, and the subsequent H1N1 bird flu, and Middle East Respiratory Syndrome outbreaks, it has been clearly proven that preventative measures to limit viral spread are the key to preventing the spread of the epidemic and controlling the epidemic. Among protective measures, preventing the virus from being transmitted from patients to medical staff or uninfected people nearby is the key to preventing the spread of the epidemic and controlling the epidemic.

Possible transmission routes of the COVID-19 virus and its evolved variants include droplet transmission, close contact transmission, and aerosol transmission in closed environments. Obviously, cutting off the transmission path of the virus is a key step in the protective measures against respiratory infectious diseases. Among the preventative measures to cut off transmission of the virus, one is passive protection against unknown sources of virus, including personal wearing masks, medical staff wearing protective clothing and other protective measures; the other is active protection against known sources of virus, including isolation measures, such as setting up isolation cabins, residential isolation, negative pressure ambulance isolation for patient transport, etc.

With regard to active isolation and protection measures, patients who need to be transported, especially severely ill patients who are in urgent need of rescue and treatment, require special medical rescue equipment in order to be transported from the patient's location to the isolation or treatment ward of the hospital. With regard to the use of special medical rescue equipment, there are two basic types available: closed and non-closed. The use of closed special equipment has many deficiencies and complications, and has been gradually abandoned by the medical system. Among non-closed special equipment, specialized containment equipment based on negative pressure has an outstanding protective effect, with reliable use and good operability, and thus such equipment is valued and widely adopted by the medical system. To this end, the Ministry of Health has put forward relevant technical requirements for the development and use of negative pressure protection equipment, and formulated relevant industry standards including the following requirements: (1) Relative pressure: When starting the negative pressure device, the relative pressure in the cabin should be −30 pa~−10 Pa. (2) High filter efficiency: the air filter's filtration rate for aerosol particles with a particle size of 0.3 microns should be greater than 99.7%. (3) Structure and composition: The air purification system should consist of an air inlet, a purification and exhaust device, a control and monitoring device. The purification and exhaust device consists of an exhaust fan, an air filter and a sterilizer. The air filter and sterilizer should be installed at the suction port of the purification and exhaust device. The air inlet and outlet should be basically arranged according to the diagonal principle of top in and bottom out, forward in and back out. The control and monitoring device should be placed in the driving cab for easy operation and control. (4) Function: Create a relative negative pressure state in the patient cabin so that the air in the cabin will not diffuse outwards at will. Reasonable arrangement of air inlets and outlets allows the air in the cabin to form a relatively stable airflow, minimizing the cross-infection between doctors and patients during transportation and transfer. The air in the cabin collectively passes through the exhaust outlet, is purified by a high-efficiency air filter device and an ultraviolet sterilization device, and then discharged out of the vehicle, ensuring environmental safety.

The transfer process from the patient's physical location to the isolation or treatment ward of the hospital is divided into three stages. The first stage is when the patient is transferred from the patient's physical location to the ambulance. The second stage is when the patient is in the ambulance. The third stage is the transfer of patients from the ambulance to the isolation or treatment ward. During these three processes, the medical staffs are close contacts of COVID-19 patients, especially when transferring the COVID-19 patients between various stages, the medical staffs are exposed to high-risk working environments. Therefore, it is necessary to ensure the absolute safety and avoidance of infection of the medical personnel within each process and at the interface between various processes.

Based on the above considerations, some enterprises have developed and produced negative pressure ambulance products specifically for the second stage when patients are in ambulances. These measures can ensure the absolute safety of medical staff against infection at this stage, but there are still five problems during actual use: I. The efficiency of air convection in the medical cabin to purify contaminated air needs to be improved, especially in cases where the space in the negative pressure ambulance cabin reaches 6-8 m³, which is a relatively large space. After the negative pressure purification system is turned on, the relative air pressure can only reach about −30 pa, and the relative efficiency is very low. II. The sealing performance of the medical cabin needs to be improved. III. The stability of the negative pressure system for heating and cooling air conditioners needs to be improved. IV. The system has poor protection for the first 100 meters. V. The system has poor protection for the last 100 meters.

With regard to the avoidance of infection and safety for medical staffs in stages 1 and 3, currently technology is absolutely safe. However, among current technologies, there are no very mature technical solutions for safety protection en route (stage 2). Existing technical solutions, are divided into negative pressure isolation cabins and semi-closed isolation devices. The negative pressure isolation cabins are cumbersome to use, uncomfortable, make administration of first aid inefficient, and offer no means of antivirus sterilization. In emergencies, such as power shortages, shortcomings such as safety hazards are likely to occur. Additionally, the degree of isolation provided by current products to patients is limited. Accordingly, such of devices and products are gradually being abandoned by medical institutions. The semi-closed isolation devices can only be used in ambulances. They cannot meet the protection requirements for the initial first aid stage, that is, the transfer of patient from the patient's physical location to the ambulance and from the ambulance to the isolation or treatment ward of the hospital. The transfer during this process still has the possibility of infecting medical staff and surrounding personnel.

SUMMARY

In view of the shortcomings of the existing technology, the purpose of the present disclosure is to provide a protective isolation hood that can play an isolation and protective role during the transfer of COVID-19 patients from home to ambulance and from ambulance to hospital isolation ward.

In order to solve the above technical problems, the present disclosure provides a protective isolation hood, comprising a fixed base cover, a rotating auxiliary cover, a base cover sliding seat and a guide rail supporting base, wherein the guide rail supporting base is connected to the base cover sliding seat, the fixed base cover is disposed on the base cover sliding seat, and the rotating auxiliary cover is rotationally arranged on the fixed base cover; a first isolation soft film is arranged at an end of the rotating auxiliary cover away from the fixed base cover, and the fixed base cover, the rotating auxiliary cover and the first isolation soft film constitute a protection space; a filter box is arranged on the fixed base cover, is located in the protection space, and is provided with a disinfection filter screen; first exhaust ports are formed in the guide rail supporting base, an exhaust fan used for discharging air in the protection space outwards is arranged in each first exhaust port, and is connected to a power supply; each first exhaust port communicates with the filter box by means of a first pipeline.

When adopting the above structure, the protective isolation hood of the present disclosure has the following advantages: during the transfer process of COVID-19 patients from their physical location to the ambulance, and from the ambulance to the isolation ward of the hospital, the patient's head is located in the protection space, and the air in the protection space is discharged by the exhaust fan from the first exhaust ports through the first pipelines, so that the air in the protection space cannot escape from gaps other than the first exhaust ports, forming a safe negative pressure environment in the protection space. Moreover, when the air passes through the filter box, the disinfection filter screen filters the aerosols in the air, wherein the filtration efficiency for particles with a diameter of 0.3 microns is greater than 99.7%, blocking the leakage of infectious sources, and ensuring the cleanness and safety of medical staff and the surrounding environment. At the same time, the disinfection filter screen can disinfect virus-containing aerosols, further improving the protective isolation effect during transportation. This prevents medical staff or ordinary people from being infected, meets the protection requirements of the initial first aid stage, improves the comfort of patients, and improves the convenience and efficiency of emergency rescue measures for medical staff during ambulance transfer, and takes into account patient comfort, full protection requirements for epidemic prevention, and convenience and efficiency of administering first aid. The present disclosure can effectively solve the absolute safety problem of medical personnel in the first and third stages, and at the same time, it can effectively improve the five practical problems that arise in the practical use of negative pressure ambulances in the second stage. It can allow medical staff to provide patients with very humane and comfortable first aid treatment in terms of effectiveness, convenience, first aid administration, etc. At the same time, it also solves the following five problems existing in existing ambulances: I. The efficiency of air convection in the medical cabin to purify contaminated air needs to be improved, especially in cases where the space in the negative pressure ambulance cabin reaches 6-8 $m^3$, which is a relatively large space. After the negative pressure purification system is turned on, the relative air pressure can only reach about −30 pa, and the relative efficiency is very low. II. The sealing performance of the medical cabin needs to be improved. III. The stability of the negative pressure system for heating and cooling air conditioners needs to be improved. IV. The system has poor protection for the first 100 meters. V. The system has poor protection for the last 100 meters.

As an improvement, the fixed base cover is provided with a second exhaust port, the second exhaust port is detachably connected to a second pipeline, and the second pipeline is externally connected to a negative pressure source outside the fixed base cover. With this structure, after the patient being sent to the ambulance or the isolation ward of the hospital, the negative pressure source is connected through the second exhaust port and the second pipeline, and stable isolation protection is performed directly through the negative pressure source.

As an improvement, a sealing sheet is connected to the fixed base cover; when the second pipeline is not connected to the second exhaust port, the sealing sheet seals the second exhaust port; when the second pipeline is connected to the second exhaust port, the second pipeline pushes the sealing sheet away from the second exhaust port and allows the second pipeline to communicate with the protection space. With this structure, when the second pipeline and the second exhaust port are not connected to each other, the exposed second exhaust port can easily cause the air in the protection space to leak out, but the sealing sheet seals the second exhaust port to prevent the air in the cover from leaking. The sealing sheet is automatically pushed open when the second pipeline is inserted, therefore there is no need to manually open it, so that it is safer and more convenient to use.

As an improvement, the present disclosure also includes a switch, wherein a sensor for sensing the second pipeline is provided at the second exhaust port, and the switch and the sensor are electrically connected to the power supply. With this structure, the sensor senses the connection of the second pipeline, when the second pipeline is not connected, the power supply is controlled through the sensor to cause the exhaust fan to rotate and start filtration and sterilization. When the second pipeline is connected, the power supply is turned off. If necessary, the exhaust fan is directly controlled through the switch to turn on or turn off.

As an improvement, the base cover sliding seat is provided with guide rails on sides thereof, and the guide rail supporting seat is provided with guide blocks on sides thereof; the guide blocks are slidingly connected to the guide rails in a horizontal direction and allow the base cover sliding seat to slide with the guide rail supporting seat; the base cover sliding seat is also provided with a locking assembly for fixing the base cover sliding seat and the guide rail supporting seat. With this structure, since the solution of the present disclosure needs to be used with a stretcher or a hospital bed, the guide rails and the guide blocks allow the base cover sliding seat to slide relative to the guide rail supporting seat, thereby driving the fixed base cover and the rotating auxiliary cover to move, making it convenient for the patient to get on and off the stretcher or hospital bed.

After the patient has laid down on the stretcher or hospital bed, the base cover sliding seat is driven to slide to move the fixed base cover and the rotating auxiliary cover to the position of the patient's head.

As an improvement, one end of the base cover sliding seat is provided with a push-pull handle and an unlocking button, the locking assembly is connected with an electric push rod, and the unlocking button is electrically connected with the electric push rod. With this structure, the base cover sliding seat can be easily pushed and pulled through the push-pull handle, and the push-pull handle and the unlocking button are located at the same end of the base cover sliding seat, which makes it convenient to directly press the unlocking button to control the electric push rod when pushing and pulling. In this way, the locking assembly can unlock the base cover sliding seat and the guide rail supporting seat, making it convenient to use.

As an improvement, the first pipeline is a telescopic pipeline. With this structure, when the base cover sliding seat slides relative to the guide rail supporting seat, the distance between the fixed base cover and the guide rail supporting seat becomes longer. At this time, the first pipeline can be stretched to prevent from the use of overly long first pipeline which occupies the space in the protection space and causes discomfort to the patient.

As an improvement, a second isolation soft film is connected between the base cover sliding seat and the guide rail supporting seat. With this structure, after the base cover sliding seat slides relative to the guide rail supporting seat, the second isolation soft film can isolate the gap between the base cover sliding seat and the guide rail supporting seat, further enhancing the protective isolation effect.

As an improvement, the fixed base cover is provided with an auxiliary cover rotating shaft, the rotating auxiliary cover is rotationally arranged on the auxiliary cover rotating shaft, and the rotating auxiliary cover is externally connected with a motor for driving the rotating auxiliary cover to rotate. With this structure, automatic control of the rotating auxiliary cover may be achieved by the motor, or alternatively, the rotating auxiliary cover may be rotated directly and manually for manual adjustment, which is more convenient to use.

As an improvement, both the fixed base cover and the rotating auxiliary cover are made of antibacterial and flame retardant materials. With this structure, the protective effect and safety of the present disclosure are further improved.

Figure 1:
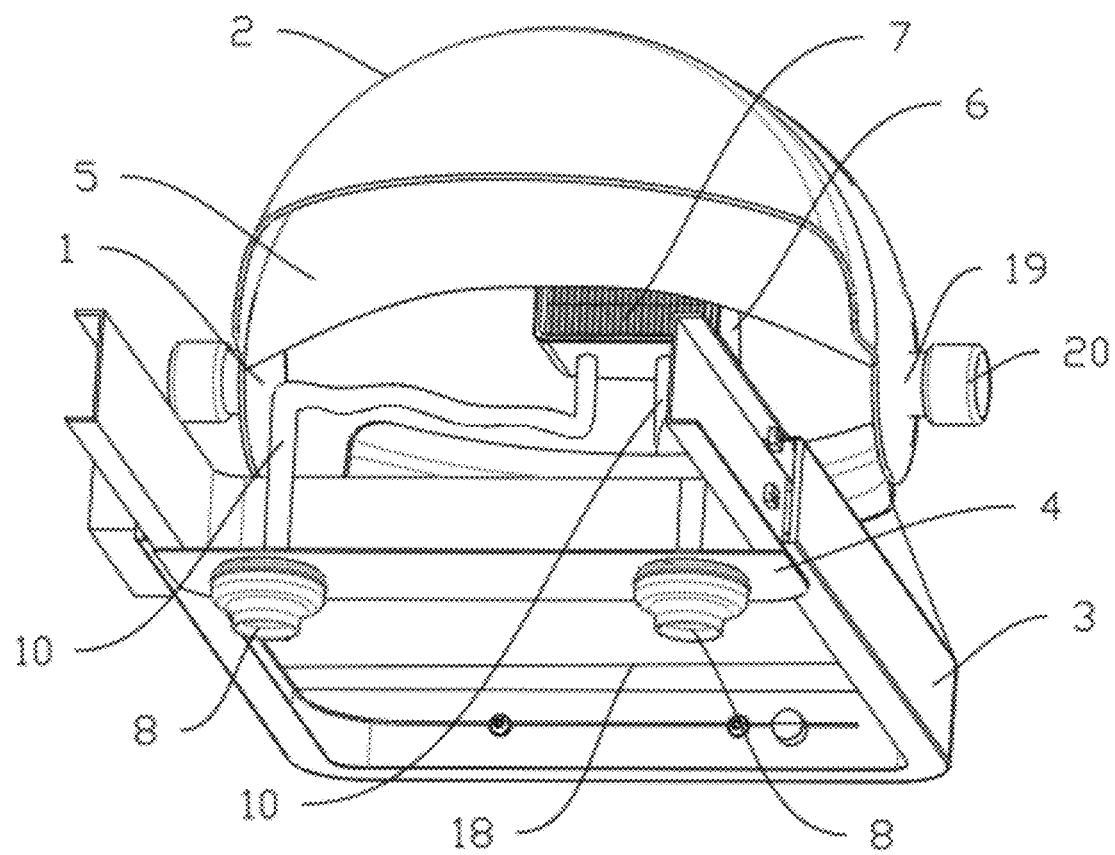
FIG. 1 is a schematic three-dimensional structural view of a protective isolation hood according to an embodiment of the present disclosure.

Reference Numerals: 1. Fixed base cover; 2. Rotating auxiliary cover; 3. Base cover sliding seat; 4. Guide rail supporting seat; 5. First isolation soft film; 6. Filter box; 7. Disinfection filter screen; 8. First exhaust port; 9. Exhaust fan; 10. First pipeline; 11. Second exhaust port; 12. Second pipeline; 13. Sealing sheet; 14. Guide rail; 15. Guide block; 16. Push-pull handle; 17. Unlocking button; 18. Second isolation soft film; 19. Auxiliary over shaft; 20. Motor.

DETAILED DESCRIPTION OF EMBODIMENTS

The protective isolation hood according to the present disclosure will be described in detail below with reference to the accompanying drawings.

As shown in FIGS. 1 to 4, there is provided a protective isolation hood (head cover) including a fixed base cover 1, a rotating auxiliary cover 2, a base cover sliding seat 3 and a guide rail supporting seat 4. The fixed base cover 1 and the rotating auxiliary cover 2 are both made of antibacterial and flame-retardant materials. The guide rail supporting seat 4 is connected to the base cover sliding seat 3. The fixed base cover 1 is located on the base cover sliding seat 3. During use, the guide rail supporting seat 4 is connected to a stretcher or hospital bed and remains relatively stationary with the stretcher or hospital bed, and it can be connected to various stretchers or hospital beds. The rotating auxiliary cover 2 is rotationally arranged on the fixed base cover 1, and a first isolation soft film 5 is arranged at one end of the rotating auxiliary cover 2 away from the fixed base cover 1. The fixed base cover 1, the rotating auxiliary cover 2 and the first isolation soft film 5 form a protection space. The fixed base cover 1 is provided with a filter box 6, and the filter box 6 is located in the protection space. The filter box 6 is provided with a disinfection filter screen 7, the guide rail supporting base 4 is provided with first exhaust ports 8, and each first exhaust port 8 is provided with an exhaust fan 9 for discharging the air in the protection space outwards. The exhaust fan 9 is connected to a power supply, and the first exhaust ports 8 and the filter box 6 are connected through first pipelines 10. In this embodiment, there are two first exhaust ports 8, two exhaust fans 9 and two first pipelines 10.

Figure 2:
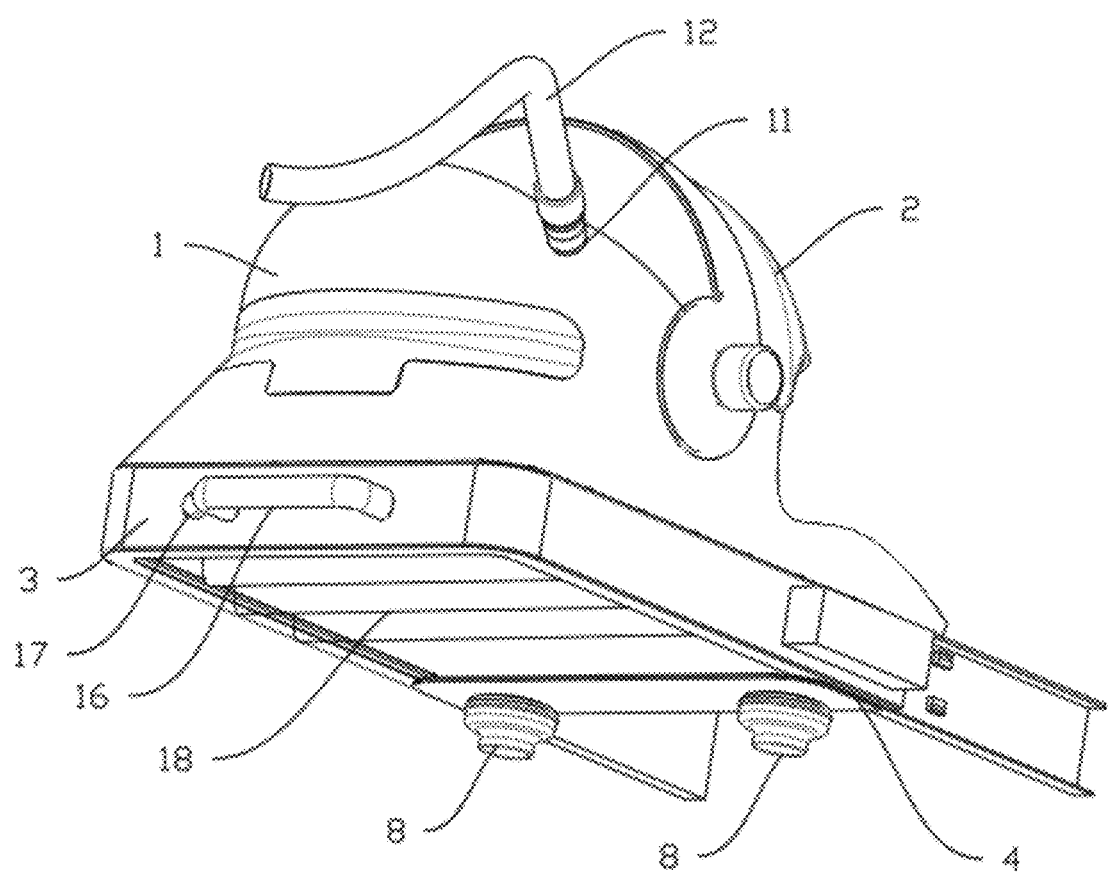
FIG. 2 is a schematic three-dimensional structural view of the protective isolation hood from another angle according to the embodiment of the present disclosure.
Figure 3:
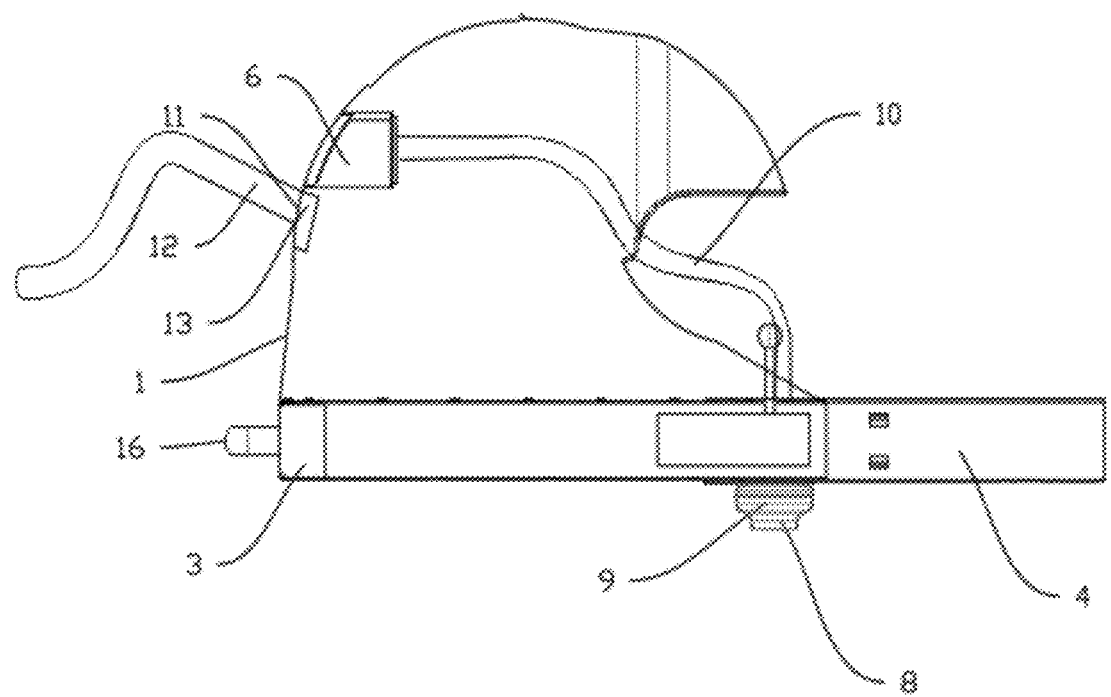
FIG. 3 is a schematic structural view of the interior of the fixed base cover in the embodiment of the present disclosure.

As shown in FIGS. 2 and 3, the fixed base cover 1 is also provided with a second exhaust port 11. The second exhaust port 11 is detachably connected to a second pipeline 12, and the second pipeline 12 can be externally connected to a negative pressure source outside the fixed base cover. A sealing sheet 13 is connected to the fixed base cover 1, and the sealing sheet 13 is located in the protection space. When the second pipeline 12 and the second exhaust port 11 are not connected to each other, the sealing sheet 13 seals the second exhaust port 11; when the second pipeline 12 is connected to the second exhaust port 11, the second pipeline 12 pushes the sealing sheet 13 away from the second exhaust port 11 and allows the second pipeline 12 to communicate with the protection space. The second exhaust port 11 is provided with a sensor for sensing the second pipeline 12. The present disclosure is also equipped with a switch. The switch and the sensor are electrically connected to the power supply for turning on or turning off the exhaust fan 9.

During the transfer of COVID-19 patients from home to the ambulance and from the ambulance to the isolation ward of the hospital, the patient's head is located in the protection space, and the air in the protection space is discharged from the first exhaust ports through the first pipeline 10 by using the exhaust fan 9, according to the path obtained by the smoke test. It forms a one-way stable negative pressure exhaust flow field, forms a safe negative pressure environment in the protection space, and when the air passes through the filter box 6, the disinfection filter screen 7 filters aerosols in the air, and the filtration efficiency for particles with a diameter of 0.3 microns is greater than 99.7%, blocking the leakage of infectious sources, ensuring the cleanliness and safety of the patient's surrounding environment, and ensuring the safety of medical staff. At the same time, the disinfection filter screen 7 in the present disclosure is a long-lasting antibacterial disinfection filter screen with self-disinfection function. It can disinfect virus-containing aerosols and can be used for up to three months. It has high disinfection reliability and further improves the protective isolation effect during the transfer process. It prevents medical staff from being infected, meets the protection requirements of the terminal first aid stage, improves the comfort of patients, and improves the convenience and efficiency of emergency rescue measures for medical staff during ambulance transfer, and takes into account patient comfort, full protection requirements for epidemic prevention, and first aid convenience and efficiency. After the patient is sent to the ambulance or the isolation ward of the hospital, the protection of the first pipeline 10 is switched to the protection of the second pipeline 12, i.e., the second pipeline 12 is inserted into the second exhaust port 11 and it is connected to the negative pressure source outside the cover. The inserted second pipeline 12 pushes open the sealing sheet 13, and then the negative pressure source outside the cover provides the stable isolation protection directly. At this time, the sensor senses the second pipeline 12. After a certain time period of delay in which it provides stable flow field, the power supply can be controlled to cut off so that the exhaust fan 9 stops rotating, and it is completely transformed into the protection control of the second pipeline 12. In order to achieve zero gap of protection and ensure no missing protection, the first pipelines 10 and the second pipeline 12 must be interlocked. After unplugging the second pipeline 12, the sensor senses that the second pipeline 12 is pulled out, the power supply is energized to cause the exhaust fan 9 to rotate. If necessary, the exhaust fan 9 can be started and stopped directly through the switch. When the second pipeline 12 is pulled out, the sealing sheet 13 automatically seals the second exhaust port 11. In this embodiment, the sealing sheet 13 is made of an elastic silicone rubber piece to achieve automatic sealing, and the sensor may be a sensing element or a travel switch.

Figure 4:
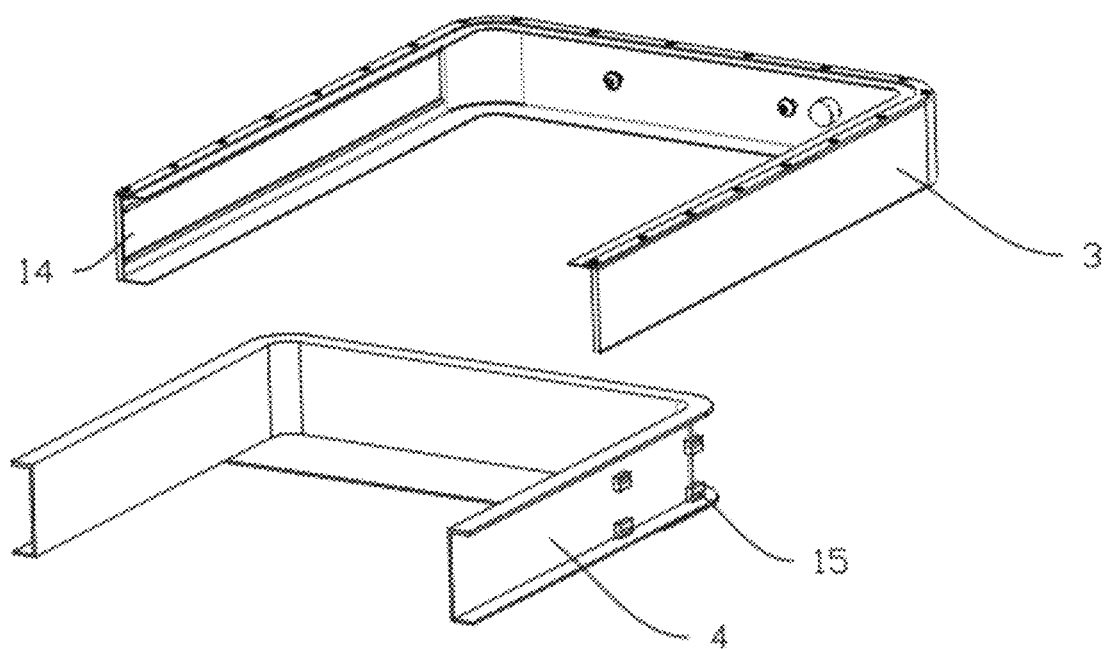
FIG. 4 is an exploded structural view of the base cover sliding seat and the guide rail supporting seat in the embodiment of the present disclosure.

As shown in FIG. 4, the base cover sliding seat 3 and the guide rail supporting seat 4 are both U-shaped, and the base cover sliding seat 3 is provided with guide rails 14 on the side, and the guide rail supporting seat 4 is provided with guide blocks 15 on the side. The guide blocks 15 is slidingly connected to the guide rails 14 in the horizontal direction and allow the base cover sliding seat 3 to slide with the guide rail supporting seat 4. The base cover sliding seat 3 is also provided with a locking assembly for fixing the base cover sliding seat 3 and the guide rail supporting seat 4; one end of the base cover sliding seat 3 is provided with a push-pull handle 16 and an unlocking button 17. The locking assembly is connected to an electric push rod, and the unlocking button 17 is electrically connected to the electric push rod; the first pipeline 10 is a telescopic pipeline, that is, the corrugated hose. A second isolation soft film 18 is connected between the base cover sliding seat 3 and the guide rail supporting seat 4. Specifically, the location of the patient lying flat on a stretcher or hospital bed is used as a reference, the left and right sides of the base cover sliding seat 3 are both provided with guide rails 14, and the left and right sides of the guide rail supporting seat 4 are both provided with guide blocks 15, and the guide rail supporting seat 4 is located in the base cover sliding seat 3, and the sliding direction of the seat cover sliding seat 3 relative to the guide rail supporting seat 4 is along the length of the stretcher or hospital bed, and the push-pull handle 16 and the unlocking button 17 are located at one end sandwiched by the left and right sides of the base cover sliding seat 3, that is, the end in the longitudinal direction. The two ends of the second isolation soft film 18 are respectively connected to the end of the base cover sliding seat 3 and the end of the guide rail supporting seat 4. The locking assembly includes a limit member and a lever; after the limit member is clamped in a limit hole in the guide rail supporting seat 4, the base cover sliding seat 3 and the guide rail supporting base 4 are fixed. After the limit member is moved out of the limit hole by turning the lever, the base cover sliding seat 3 can slide. By pressing the unlocking button 17, it controls the electric push rod to move the lever. The specific structure of the locking assembly is of an existing technology and will not be described in detail here.

The fixed base cover 1 is provided with an auxiliary cover rotating shaft 19. The rotating auxiliary cover 2 is rotatably mounted on the auxiliary cover rotating shaft 19. The rotating auxiliary cover 2 is externally connected with a motor 20 for driving the rotating auxiliary cover 2 to rotate. Since the present disclosure needs to be used with a stretcher or a hospital bed, the arrangement of the guide rails 14 and the guide blocks 15 allows the base cover sliding seat 3 to slide relative to the guide rail supporting seat 4, thereby driving the fixed base cover 1 and the rotating auxiliary cover 2 to move, to facilitate the patient to get on and off the stretcher or hospital bed. After the patient has laid down on the stretcher or hospital bed, the base cover sliding seat 3 is driven to slide to move the fixed base cover 1 and the rotating auxiliary cover 2 to the position of the patient's head. After the base cover sliding seat 3 slides relative to the guide rail supporting base 4, the distance between the fixed base cover 1 and the guide rail supporting base 4 becomes longer. At this time, the first pipeline 10 is stretched. The use of the telescopic first pipeline 10 can prevent from the use of overly long first pipeline 10 which occupies the space in the protection space and causes discomfort to the patient. After the base cover sliding seat 3 slides relative to the guide rail supporting seat 4, the second isolation soft film 18 can isolate large gap between the base cover sliding seat 3 and the guide rail supporting base 4, further enhancing the protective isolation effect. Compared with the closed negative pressure isolation cabin, the negative pressure isolation cabin in the prior art is powered by batteries and is not suitable for tasks requiring long-distance transportation. Moreover, the discharged air is only filtered and not disinfected, so there is still a risk of infection. In addition, the patient is in a completely enclosed space during the transfer process, making it impossible to carry out efficient and complex treatment, and the patient's comfort is poor, and it is not suitable for special groups suffering from claustrophobia. However, the present disclosure uses a semi-closed isolation device, if it is provided to the ambulance, it can be powered by the vehicle's power supply system. It is suitable for long-distance and long-term transportation. The discharged air is not only highly filtered but also disinfected. The semi-enclosed space allows to carry out efficient and complex treatment, and it is also suitable for those special groups suffering from claustrophobia. In addition, compared with the existing semi-closed isolation device, the present disclosure increases the terminal first aid stage, that is, from the location of the patient to the ambulance, and from the ambulance to the isolation ward of the hospital, further improving the protective isolation effect. The patients can be efficiently isolated in a small local space in the ward. The embodiments of the present disclosure have been described in detail above with reference to the accompanying drawings. However, the present disclosure is not limited to the above-mentioned embodiments. All other embodiments obtained by those skilled in the art without making creative efforts belong to the scope of the present disclosure.

What is claimed is:

1. A protective isolation hood, comprising a fixed base cover (1), a rotating auxiliary cover (2), a base cover sliding seat (3) and a guide rail supporting base (4), wherein the guide rail supporting base (4) is connected to the base cover sliding seat (3), the fixed base cover (1) is disposed on the base cover sliding seat (3), and the rotating auxiliary cover (2) is rotationally arranged on the fixed base cover (1); a first isolation soft film (5) is arranged at an end of the rotating auxiliary cover (2) away from the fixed base cover (1), and the fixed base cover (1), the rotating auxiliary cover (2) and the first isolation soft film (3) constitute a protection space; a filter box (6) is arranged on the fixed base cover (1), is located in the protection space, and is provided with a disinfection filter screen (7); first exhaust ports (8) are formed in the guide rail supporting base (4), an exhaust fan (9) used for discharging air in the protection space outwards is arranged in each first exhaust port (8), and is connected to a power supply; each first exhaust port (8) communicates with the filter box (6) by means of a first pipeline (10), wherein the fixed base cover (1) is provided with a second exhaust port (11), the second exhaust port (11) is detachably connected to a second pipeline (12), and the second pipeline (12) is externally connected to a negative pressure source outside the fixed base cover (1), wherein a sealing sheet (13) is connected to the fixed base cover (1); when the second pipeline (12) is not connected to the second exhaust port (11), the sealing sheet (13) seals the second exhaust port (11); when the second pipeline (12) is connected to the second exhaust port (11), the second pipeline (12) pushes the sealing sheet (13) away from the second exhaust port (11) and allows the second pipeline (12) to communicate with the protection space.

2. The protective isolation hood according to claim 1, further comprising a switch, wherein a sensor for sensing the second pipeline (12) is provided at the second exhaust port (11), and the switch and the sensor are electrically connected to the power supply.

3. The protective isolation hood according to claim 1, wherein the base cover sliding seat (3) is provided with guide rails (14) on sides thereof, and the guide rail supporting seat (4) is provided with guide blocks (15) on sides thereof; the guide blocks (15) are slidingly connected to the guide rails (14) in a horizontal direction and allow the base cover sliding seat (3) to slide with the guide rail supporting seat (4); the base cover sliding seat (3) is also provided with a locking assembly for fixing the base cover sliding seat (3) and the guide rail supporting seat (4).

4. The protective isolation hood according to claim 3, wherein one end of the base cover sliding seat (3) is provided with a push-pull handle (16) and an unlocking button (17), the locking assembly is connected with an electric push rod, and the unlocking button (17) is electrically connected with the electric push rod.

5. The protective isolation hood according to claim 3, wherein the first pipeline (10) is a telescopic pipeline.

6. The protective isolation hood according to claim 3, wherein a second isolation soft film (18) is connected between the base cover sliding seat (3) and the guide rail supporting seat (4).

7. The protective isolation hood according to claim 1, wherein the fixed base cover (1) is provided with an auxiliary cover rotating shaft (19), the rotating auxiliary cover (2) is rotationally arranged on the auxiliary cover rotating shaft (19), and the rotating auxiliary cover (2) is externally connected with a motor (20) for driving the rotating auxiliary cover (2) to rotate.

8. The protective isolation hood according to claim 1, wherein both the fixed base cover (1) and the rotating auxiliary cover (2) are made of antibacterial and flame retardant materials.

* * * * *